(12) United States Patent
Reutter et al.

(10) Patent No.: US 7,217,698 B2
(45) Date of Patent: May 15, 2007

(54) USE OF MANNOSAMINE DERIVATIVES FOR THE STIMULATION OF NEURITE GROWTH

(75) Inventors: Werner Reutter, Berlin (DE); Rüdiger Horstkorte, Berlin (DE); Carolin Horstkorte, Berlin (DE)

(73) Assignee: Dompatent von Kreisler Selting Werner (DE)

( * ) Notice: Subject to any disclaimer, the term of this patent is extended or adjusted under 35 U.S.C. 154(b) by 206 days.

(21) Appl. No.: 10/490,934

(22) PCT Filed: Sep. 25, 2002

(86) PCT No.: PCT/EP02/10768

§ 371 (c)(1),
(2), (4) Date: Sep. 7, 2004

(87) PCT Pub. No.: WO03/028709

PCT Pub. Date: Apr. 10, 2003

(65) Prior Publication Data

US 2005/0107333 A1    May 19, 2005

(30) Foreign Application Priority Data

Sep. 26, 2001   (DE) ................. 101 47 382
Jan. 29, 2002   (DE) ................. 102 03 308

(51) Int. Cl.
*A61K 31/70* (2006.01)
*A61K 31/7028* (2006.01)

(52) U.S. Cl. ............................ 514/25; 514/23; 536/4.1

(58) Field of Classification Search ............... 514/25, 514/23; 536/4.1
See application file for complete search history.

(56) References Cited

U.S. PATENT DOCUMENTS 6,274,568 B1 *   8/2001   Schnaar et al. ............... 514/62

FOREIGN PATENT DOCUMENTS

| DE | 19738484 A | 4/1999 |
| WO | WO 00/07602 A | 2/2000 |
| WO | WO 00/29567 | 5/2000 |

OTHER PUBLICATIONS

Charter et al. "Differential effects of unnatural sialic acids on the polysialylation of the neural cell adhesion molecule and neuronal behavior," J. Biol. Chem. 277(11) 9255-9261 (2002).
Ogiso et al. "Lack of cell density-dependent changes in gangliosides of rat primary culture neurons," Dev. Neuroscience 14(3) 247-255 (1992).
Grünholz et al., "Inhibition of in vitro biosynthesis of N-acetylneuraminic acid by n-acyl-and n-alkyl-2-amino-2-dexyhexoses" Carbohydrate Research, 96:259-270 (1981).
Kayser et al., "Incorporation of N-acyl-2-amino-2deoxy-hexoses into glycosphingolipids of the pheochromocytoma cell lin PC 12," FEBS 301(2):137-140 (1992).
Schauer et al., "Biochemistry and role of sialic acids," Biology of the sialic acids, Rosenberg (ed.) Plenum Press, New York, 1995.
Varki, "Mini Review-Diversity in the sialic acids," Glycobiology 2(1):25-40 (1992).

* cited by examiner

*Primary Examiner*—Shaojia Anna Jiang
*Assistant Examiner*—Michael C. Henry
(74) *Attorney, Agent, or Firm*—Needle & Rosenberg, P.C.

(57) ABSTRACT

The present invention relates to the use of peracylated N-acyl-mannosamine derivatives for the preparation of a medicament for stimulating neurite growth.

12 Claims, 3 Drawing Sheets

USE OF MANNOSAMINE DERIVATIVES FOR THE STIMULATION OF NEURITE GROWTH

CROSS REFERENCE TO RELATED APPLICATIONS

The present application claims priority to German Application No. 10147382.6, filed Sep. 26, 2001 and German Application No. 10203308.0, filed Jan. 29, 2002, which applications are incorporated herein fully by this reference.

The present invention relates to the use of N-acyl-mannosamine derivatives, especially N-propanoyl-1,3,4,6-O-tetraacetylmannosamine and N-cyclopropyl-carbonyl-1,3,4,6-O-tetracyclopropylcarbonylmannosamine for the stimulation of neurite growth.

BACKGROUND OF THE INVENTION

Sialic acids are carbohydrates which form a family of about 40 naturally occurring derivatives of neuraminic acid and which all except one are N-acylated (Schauer et al., 1995; Varki, 1992). They are distinguished from another by N and/or O substituents. N substituents are primarily acetyl and glycolyl groups. O substituents are, among others, acetyl, lactoyl, methyl, sulfate and phosphate groups. The most abundant representative of sialic acids is N-acetylneuraminic acid (NeuNAc), which is the precursor of all other sialic acids. Sialic acids are the terminal monosaccharides of complex N-glycans and many O-glycanes of glycoproteins as well as gangliosides.

By different modifications and binding types, the neuraminic acids contribute to the structural variety of glycoconjugates and have a great influence on numerous biological processes.

While sialinic acids play an important role in various biological processes, until recently, nothing was known about the importance of their N-acetyl or N-glycolyl side chain in these processes. The physiological precursor of all natural sialinic acids is N-acetylmannosamine. By the application of non-physiological N-acyl-mannosamines or glucosamines whose side chain is extended by one or more methylene groups, the corresponding neuraminic acids are biosynthesized (Grunholz et. al., 1981; Kayser et al. 1992).

A precursor such as N-propanoylmannosamine (ManNProp) is metabolized into N-propanoylneuraminates and subsequently, as N-propanoyineuraminic acid (NeuNProp), it is incorporated into the membrane proteins of the cells as well as into the serum glycoproteins (gangliosides) (Kayser et al., 1992).

Cell culture experiments have shown that biological processes such as viral infections and cell proliferation are permanently influenced by thus modified neuraminic acids.

DE 197 38 484 discloses the use of N-propanoylmannosamine, N-isopropanoyl-mannosamine and/or N-cyclopropanoylmannosamine (i.e., more correctly, N-cyclopropylcarbonylmannosamine) for the preparation of a medicament for myelinization and remyelinization. The capability of the above mentioned mannosamine derivatives of effecting myelinization and remyelinization is based on their property of being stimulators of oligodendrocytes.

Further, WO 00/07602 describes that particular N-acyl-mannosamines (such as N-acetyl-, N-propanoyl-, N-glycolyl-, N-formylmannosamines) are suitable for the modulation of neuronal growth or for the enhancement or inhibition of neurite growth. However, these compounds have the drawback that their effectiveness is rather low. On the other hand, WO 00/07602 also discloses O-acylated derivatives of the above mentioned compounds; in particular, N-glycolylmannosamine pentaacetate is mentioned. However, all the glycolylmannosamine derivatives have the drawback of being antigenic.

Surprisingly, it has been found that special N- and O-acylated mannosamine compounds can stimulate neurite growth significantly better as compared to the compounds of WO 00/07602. N-propanoyl- and N-cyclopropylcarbonyltetraacetylmannosamine have proven particularly suitable (among the non-O-acylated compounds N-propanoylmannosamine has been found to be most effective.

SUMMARY OF THE INVENTION

Therefore, the present invention relates to
(1) the use of N-acylmannosamine derivatives of formula (I)

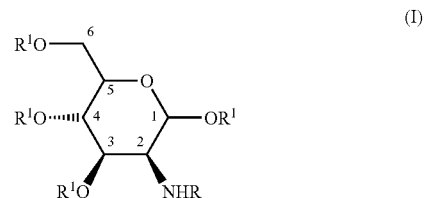

wherein
R is an acyl residue, especially an acetyl (—CO—CH$_3$), propanoyl (—CO—C$_2$H$_5$), butanoyl (—CO—C$_3$H$_7$), pentanoyl (—CO—C$_4$H$_9$), hexanoyl (—CO—C$_5$H$_{11}$), cyclopropyl-carbonyl (—CO—C$_3$H$_5$), crotonoyl (—CO—CH=CH—CH$_3$), levulinoyl (—CO—CH$_2$—CH$_2$—CO—CH$_3$) or azidoacetyl residue (—CO—CH$_2$—N$_3$); and
each R$^1$ independently represents an acyl residue, especially an acetyl residue; for the preparation of a medicament for stimulating neurite growth;
(2) a compound of formula (I), wherein R is a cyclopropylcarbonyl residue, and R$^1$ represent acyl residues;
(3) a pharmaceutical composition comprising the compound defined in (2) above;
(4) a process for the preparation of the compound defined in (2) above, comprising the reacting of mannosamine with an activated cyclopropylcarbonyl compound; and
(5) a method for stimulating neurite growth in mammals, especially humans, comprising administration of an acyl-mannosamine derivative as defined in (1) to said mammals (preferably to humans).

BRIEF DESCRIPTION OF THE FIGURES

The invention is further illustrated by the following FIGS. 1 to 3.

DETAILED DESCRIPTION OF THE INVENTION

Figure 1:
FIG. 1: On collagen I, PC12 cells were incubated for two days with 100 ng of NGF, followed by fixation and staining.
Figure 2:
FIG. 2: On collagen I, PC12 cells were incubated for two days with 100 ng of NGF and 5 mM N-propanoylmannosamine, followed by fixation and staining.

According to the present invention, the term "mannosamine derivatives" comprises all derivatives of mannosamine familiar to the skilled person which are derived from this compound and which contain "mannosamine" in their names. The mannosamine derivatives comprise both D and L forms of mannosamine, and a mixture of the D and L forms. Also included are the pure α and β anomers of the mannosamine derivatives and mixtures thereof.

In the mannosamine compound of formula (1), the acyl residue in the definition of $R^1$ may be any acyl residue familiar to the skilled person. However, it is preferred that $R^1$, like R, is an acetyl, propanoyl (—CO—$C_2H_5$), butanoyl (—CO—$C_3H_7$), pentanoyl (—CO—$C_4H_9$), hexanoyl (—CO—$C_5H_{11}$), cyclopropylcarbonyl (—CO—$C_3H_5$), crotonoyl (—CO—CH═CH—$CH_3$), levulinoyl (—CO—$CH_2$—$CH_2$—CO—$CH_3$) or azido-acetyl residue (—CO—$CH_2$—$N_3$), wherein R is more preferably a propanoyl, isopropanoyl, butanoyl or cyclopropylcarbonyl residue, and $R^1$ are acetyl residues.

According to the present invention, the residues comprise butanoyl (—CO—$C_3H_7$), pentanoyl (—CO—$C_4H_9$) and hexanoyl (—CO—$C_5H_{11}$), and in addition to the unbranched residues also their constitutional isomers known to the skilled person, such as isobutanoyl (—CO—CH—$(CH_3)_2$), isopentanoyl (—CO—$CH_2$—CH$(CH_3)_2$), 2-methylbutanoyl (—CO—CH$(CH_3)$—$C_2H_5$) etc.

Further, according to the present invention, the term "crotonoyl" (—CO—CH═CH—$CH_3$) comprises the two possible geometric isomers, i.e., both the E and the Z forms, which are known to the skilled person.

In a special embodiment of (1), 1-N-propanoyl-3,4,6-O-tetraacetylmannosamine is employed for the stimulation of neurite growth.

The formulation of the medicament according to the invention for stimulating neurite growth according to (1) or the formulation of the pharmaceutical composition (3) may be effected by methods known to the skilled person.

In addition to the compound of formula (I), these medicaments/compositions may also contain other pharmaceutically acceptable compounds which are familiar to the skilled person, such as carriers, diluents, etc.

The medicaments (1) are suitable for the treatment of CNS-neurodegenerative diseases, especially Alzheimer's and Parkinson's diseases. Similarly, the method (5) is suitable for treating said diseases.

The pharmaceutical composition (3) can be employed both for the stimulation of neurite growth and for myelinization and remyelinization (see DE-A-197 38 484). In addition, the compounds (2) may also be employed for the preparation of recombinant glycoproteins as described in WO 00/29567.

The preparation process according to embodiment (4) of the invention comprises the reaction of the mannosamine with an activated cyclopropylcarbonyl compound. Then, to prepare pentacyclopropylcarbonylmannosamine, purification of the product from the reaction mixture of this (first) acylation step is immediately effected. If derivatives are desired in which acyl residues other than cyclopropylcarbonyl are present, a mild saponification of the reaction mixture is first effected, followed by a second acylation step with suitable activated acyl derivatives. Suitable activated acyl compounds and cyclopropylcarbonyl compounds include anhydrides, acid anhydrides, activated esters etc. Suitable solvents for the acylation reaction include polar aprotic solvents, such as pyridine, etc. The reaction temperature for the acylation steps is from 0 to 30° C., and the reaction time is from 30 min to 24 h.

In the method (5) of the present invention, the compound (I) is administered together with suitable carriers and diluents. The administration may be effected via any possible route (intravenously, orally, etc.). The amount of compound (I) to be administered depends, in particular, on the patient's body weight and on the route of administration and is individually determined by the attending physician.

The invention will now be illustrated in more detail by the following Examples, which are, however, not to be construed as to limit the invention.

EXAMPLES

Example 1

Influence of N-propanoylmannosamine (Hereinafter "ManNProp") on PC12 Cells After Stimulation with the Growth Factor NGF It is known that stimulation with nerve growth factor (NGF) causes neuronal differentiation in PC12 cells. At an NGF concentration of 250 ng/ml and after three days of incubation, the PC12 cells already form a network of neurites.

In order to examine whether the addition of ManNProp has an influence on the neurite formation by PC12 cells, the suitable neurite lengths for different incubation times were first titrated with different NGF concentrations. At an NGF concentration of 100 ng and an incubation time of two days, the cells formed neurites whose length were double the diameter of their cell. Under such conditions, the further course of the experiments was set up.

The cells were plated with a constant number of cells on culture chambers which consisted of four chambers and were coated with collagen I (col.), poly-D-lysine (PDL) or laminin, and incubated under three different sets of conditions. Each variation was represented in duplicate.

In the first chamber, the PC12 cells were incubated with 5 mM ManNProp, and in the second chamber, they were incubated with 100 ng of NGF. In the third chamber, 100 ng of NGF plus 5 mM ManNProp was added to the cells. The first and second chambers served as a reference control for the cells under the influence of NGF and ManNProp. For each experiment, three culture chambers were sown in duplicate. After two days of incubation, the cells were fixed with paraformaldehyde, stained with crystal violet and washed with water.

For evaluation, various segments were photographed and measured according to a random choice principle. For the evaluation, only the cells stimulated with NGF which served as a control and the cells stimulated with NGF plus ManNProp were considered.

Each bar represents three experiments performed on three different days. The relative neurite length was established by CAPA (computer-assisted process analysis), and the data were integrated by means of Delta Graph.

Figure 3:
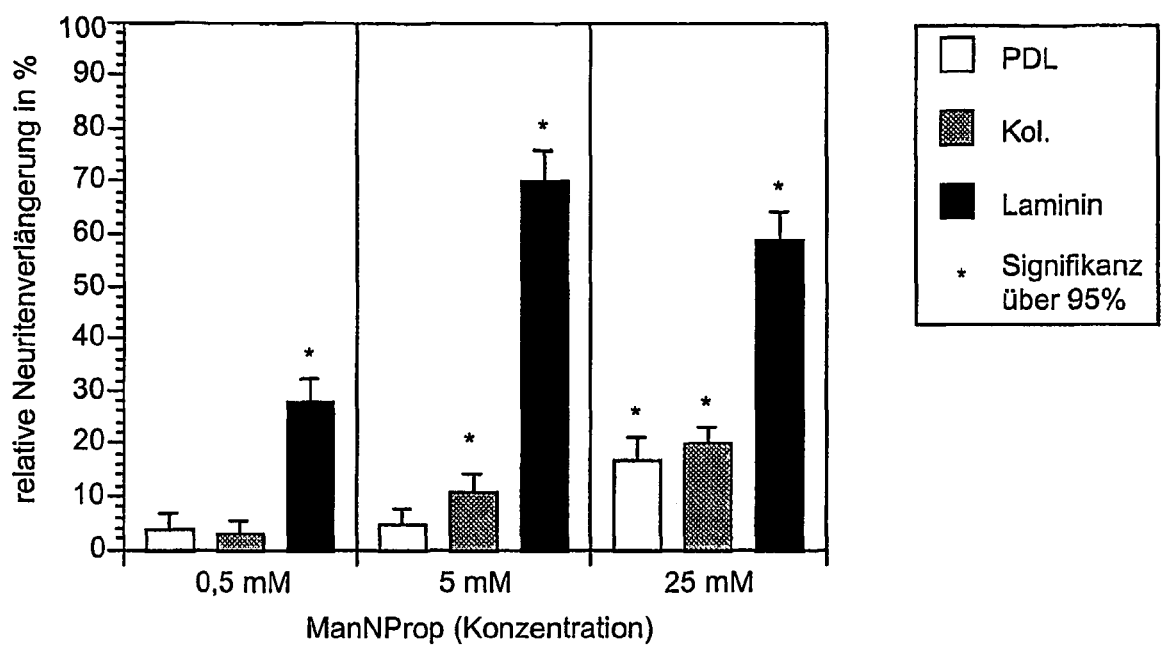
FIG. 3 shows the influence of the addition of N-propanoylmannosamine on neurite formation.

All experiments shown here were independently performed on different days. The values from Table 1 were additionally represented graphically in FIG. 3.

TABLE 1

Enhancement of neurite growth in percent relative to the control

|  | PDL | Col. | Laminin | sd PDL | sd Col. | sd Laminin |
|---|---|---|---|---|---|---|
| 0.5 mM | 4 | 3 | 28 | 2.7 | 2.4 | 4.3 |
| 5 mM | 5 | 11 | 70 | 2.6 | 3 | 5.7 |
| 25 mM | 17 | 20 | 59 | 3.9 | 2.9 | 5.2 |

The invention claimed is:

1. A compound of formula

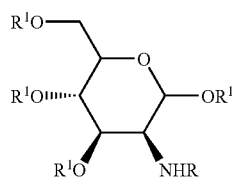

wherein R is a cyclopropylcarbonyl residue, and each $R^1$ independently represents acyl residues.

2. A pharmaceutical composition comprising the compound according to claim 1.

3. A process for the preparation of the compound according to claim 1, comprising reacting mannosamine with an activated cyclopropylcarbonyl compound chosen from cyclopropylcarbonyl anhydrides, acid anhydrides, and activated esters to form a product wherein R and each $R^1$ are cyclopropylcarbonyl.

4. A process for the preparation of the compound according to claim 1, comprising:
   a) reacting mannosamine with an activated cyclopropylcarbonyl compound chosen from cyclopropylcarbonyl anhydrides, acid anhydrides, and activated esters to form a product;
   b) purifying the product obtained in step (a);
   c) saponifying the purified product obtained in step (b);
   d) reacting the saponified product obtained in step (c) with an activated acyl compound chosen from activated acyl anhydrides, acid anhydrides, and activated esters, to form a compound wherein R is cyclopropylcarbonyl and $R_1$ is an acyl unit other than cyclopropylcarbonyl.

5. A method for stimulating neurite growth, comprising administering to a mammal with A CNS-neurodegenerative disease the compound according to claim 1, wherein the CNS-neurodegenerative disease is Alzheimer's or Parkinson's disease.

6. A method of treating a mammal with a CNS-neurodegenerative disease, wherein the neurodegenerative disease is Alzheimer's or Parkinson's disease, comprising administering the compound according to claim 1.

7. A method of treating a mammal with a CNS-disease comprising administering the compound according to claim 1.

8. A method according to claim 7, wherein the CNS-neurogenerative disease is Alzheimer's disease.

9. A method according to claim 7, wherein the CNS-neurogenerative disease is Parkinson's disease.

10. A compound according to claim 1, wherein each $R^1$ is an acyl residue chosen from acetyl, propanoyl, isopropanoyl, butanoyl, isobutanoyl, pentanoyl, isopentanoyl, hexanoyl, 2-methylbutanoyl, cyclopropylcarbonyl, crotonoyl, levulinoyl, or azidoacetyl.

11. A compound according to claim 10, wherein each $R^1$ is acetyl.

12. A compound according to claim 10, wherein each $R^1$ is cyclopropylcarbonyl.

* * * * *